United States Defensive Publication [19] (H) [11] T101,003

Watson [43] Sep. 1, 1981

[54] PREVENTATIVE THERAPY AGAINST HUMAN CANCER

[76] Inventor: Shane A. Watson, 7 Bragge St., Frankston, Victoria, Australia, 3199

[21] Appl. No.: 26,811

[22] Filed: Apr. 4, 1979

[51] Int. Cl.[2] ..... A61K 31/195

[52] U.S. Cl. ..... 424/319

[57] ABSTRACT

A method for prophylaxis against human cancer which comprises the administration of chelating or complexing agents capable of removing from the human body the various isotopic forms of lead and their radioactive precursors.

3 Claims, No Sheets Drawing,

11 Pages Specification

The file of this unexamined application may be inspected and copies thereof may be purchased (849 O.G. 1221, Apr. 9, 1968).